(12) United States Patent  
Falahee et al.

(10) Patent No.: US 8,747,408 B2  
(45) Date of Patent: *Jun. 10, 2014

(54) BONE FIXATION IMPLANT SYSTEM AND METHOD

(75) Inventors: Mark Falahee, Ann Arbor, MI (US); Phil Reed, Davie, FL (US); Doris Blake, Delray Beach, FL (US); Trace R Cawley, Boca Raton, FL (US)

(73) Assignee: US Spine, Inc., Salt Lake City, UT (US)

( * ) Notice: Subject to any disclaimer, the term of this patent is extended or adjusted under 35 U.S.C. 154(b) by 18 days.

This patent is subject to a terminal disclaimer.

(21) Appl. No.: 13/216,087

(22) Filed: Aug. 23, 2011

(65) Prior Publication Data

US 2012/0035613 A1 Feb. 9, 2012

Related U.S. Application Data

(63) Continuation of application No. 12/122,498, filed on May 16, 2008, now Pat. No. 8,002,812, which is a continuation-in-part of application No. 10/973,524, filed on Oct. 26, 2004, now Pat. No. 7,563,275, which is a continuation-in-part of application No. 10/683,076, filed on Oct. 10, 2003, now Pat. No. 7,608,094.

(60) Provisional application No. 60/417,543, filed on Oct. 10, 2002, provisional application No. 60/938,886, filed on May 18, 2007.

(51) Int. Cl.  
*A61B 17/70* (2006.01)

(52) U.S. Cl.  
USPC ............ 606/86 A; 606/99; 606/104; 606/247; 606/328

(58) Field of Classification Search  
USPC .............. 606/86 A, 99, 104, 247; 227/15, 30, 227/153; 81/125, 456  
See application file for complete search history.

(56) References Cited

U.S. PATENT DOCUMENTS 5,690,632 A * 11/1997 Schwartz et al. ............. 606/302  
2002/0004661 A1 * 1/2002 Sevrain et al. ................. 606/73

* cited by examiner

*Primary Examiner* — Nicholas Woodall  
(74) *Attorney, Agent, or Firm* — Phillips Ryther & Winchester; Matthew D. Thayne

(57) ABSTRACT

In one embodiment, a bone-fastening system includes a handle, a barrel assembly connected to the handle, and a bridge assembly connected to the barrel assembly. The bridge assembly may be configured to receive a first connector element and a second connector element in axial alignment with the first connector element so as to receive a fastening element between the first and second connector elements. The system may also include a control configured to, upon actuation, approximate the first connector element and the second connector element so as to apply compressive pressure to bone portions positioned between the first connector element and the second connector element. A drive mechanism configured to advance the fastening element through the bone portions and connect the first connector element with the second connector element to fasten the bone portions under compression may also be provided with the system.

19 Claims, 27 Drawing Sheets

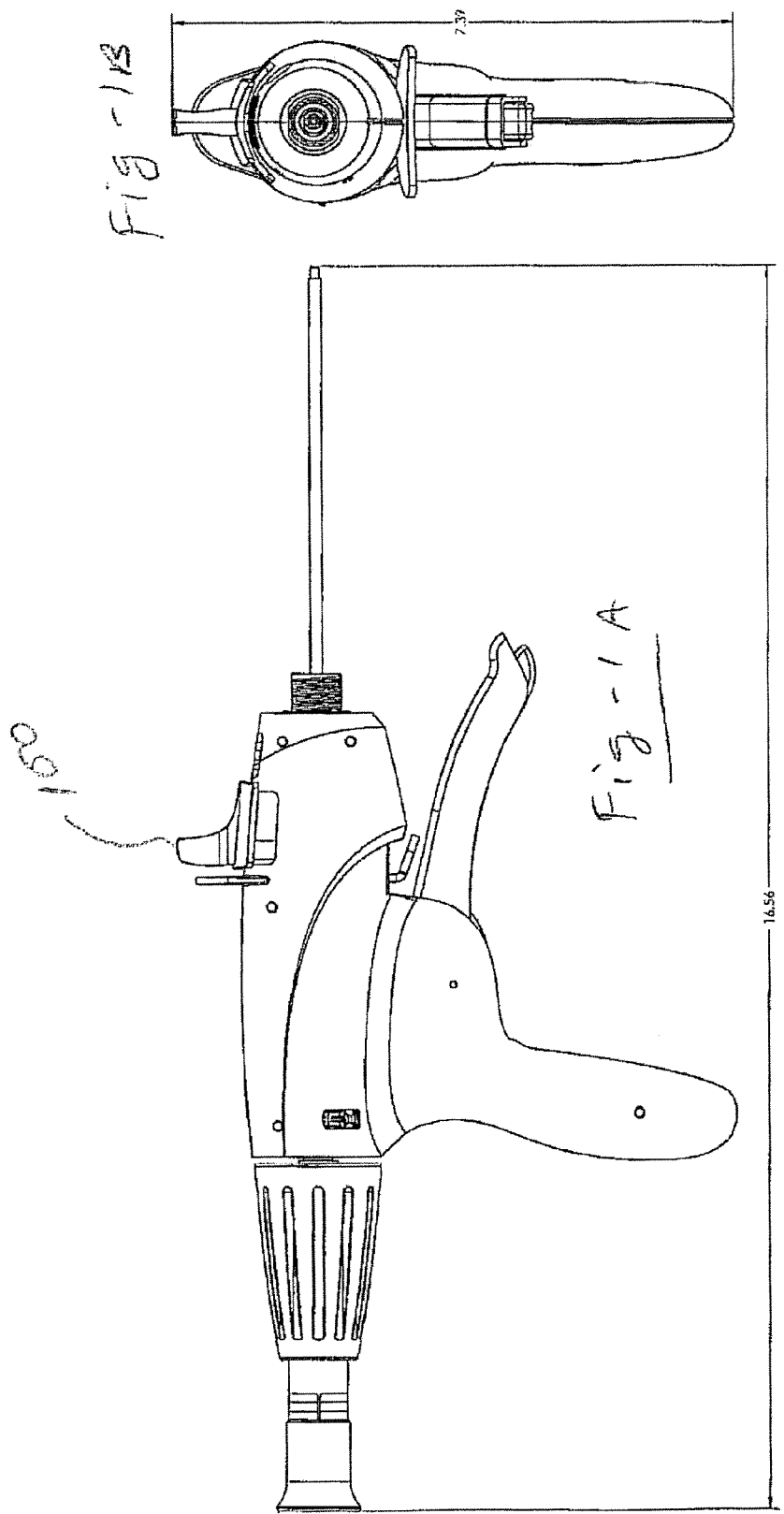

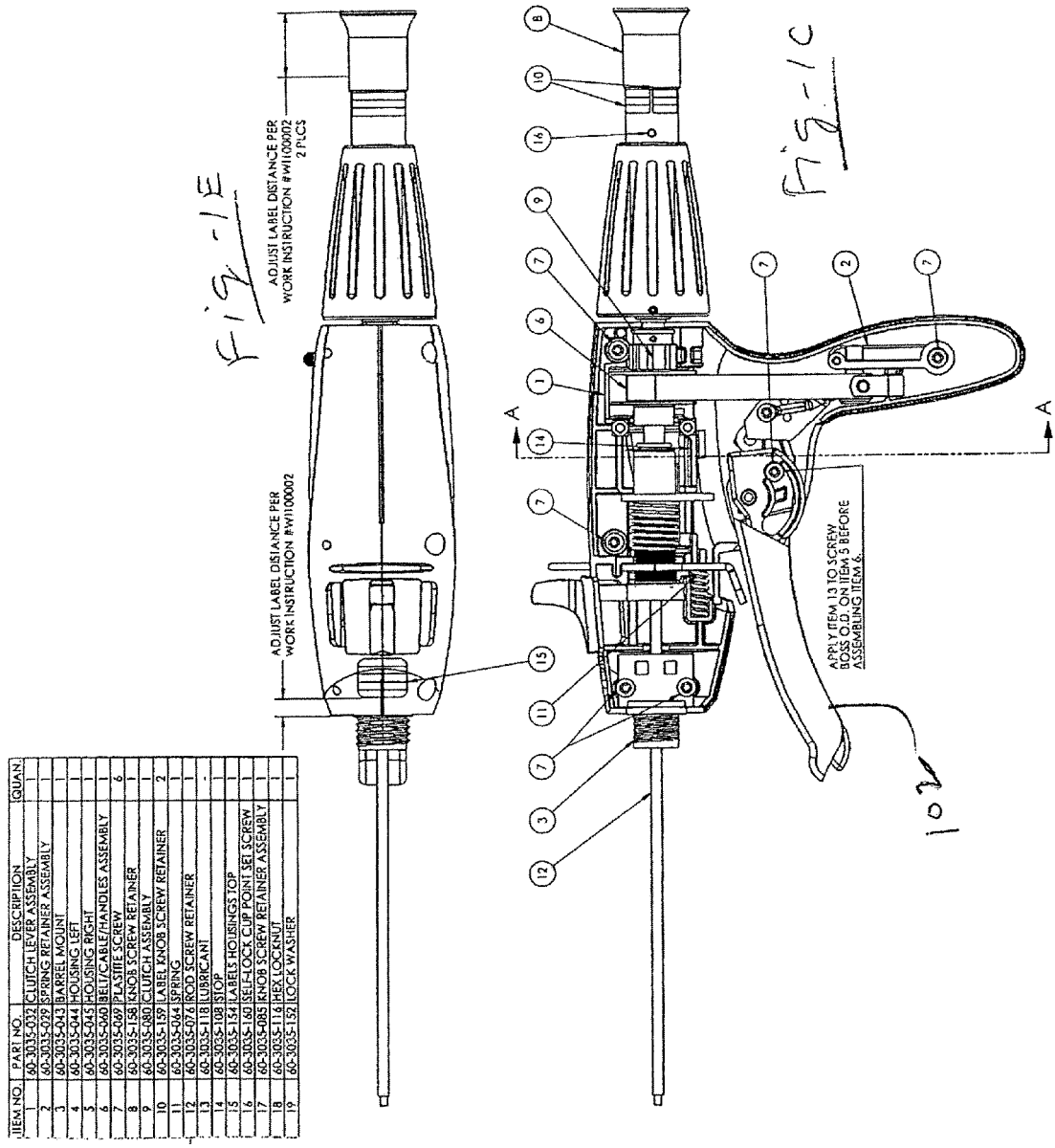

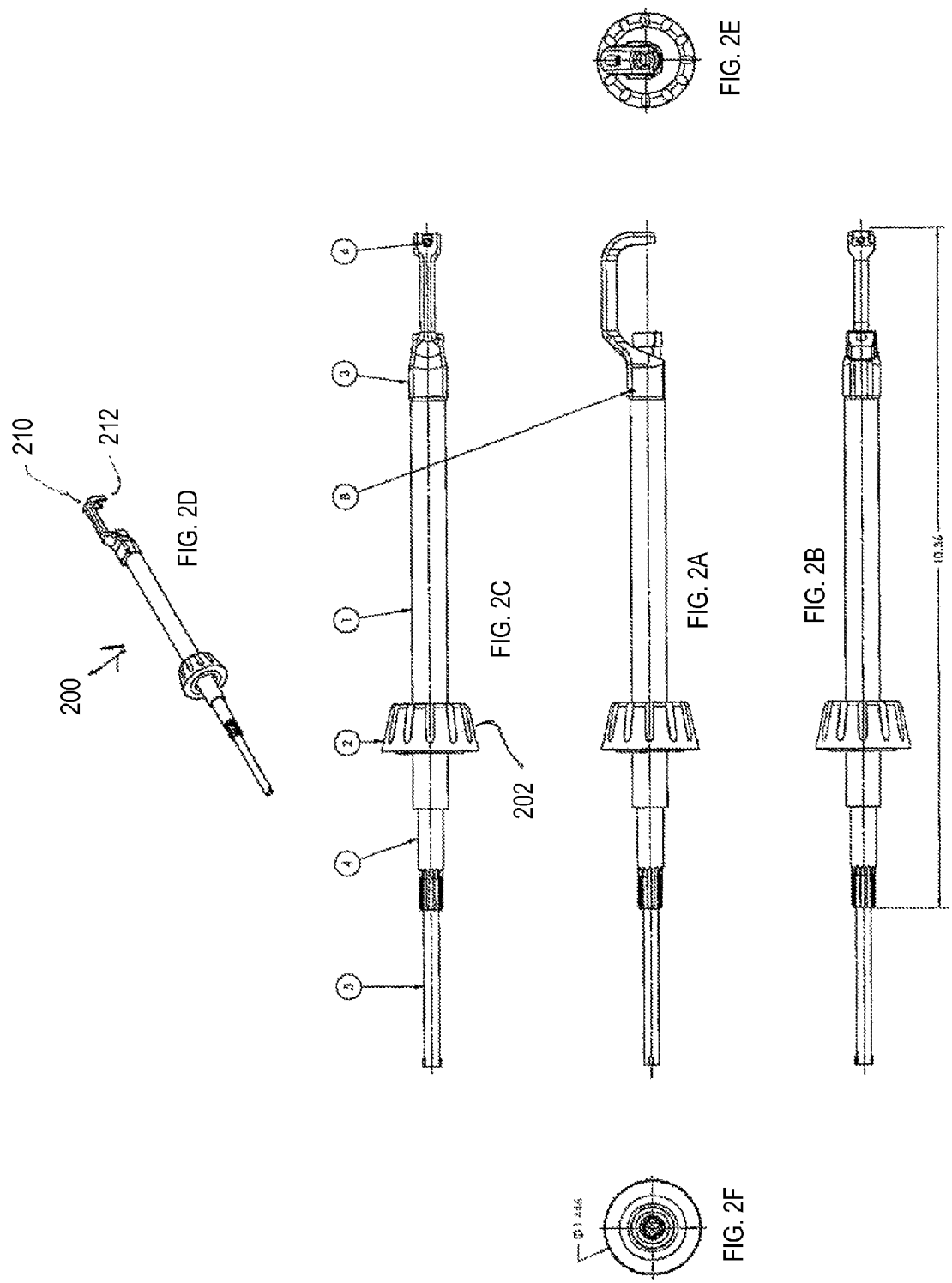

| ITEM 1 TRANSFACET DISPOSABLE BARREL ASSEMBLY | ITEM 2 SCREW | ITEM 3 NUT | ITEM 4 WASHER | ITEM 5 RETAINER |
|---|---|---|---|---|

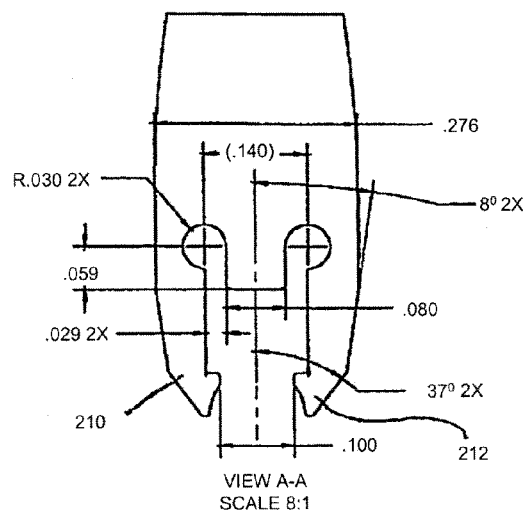
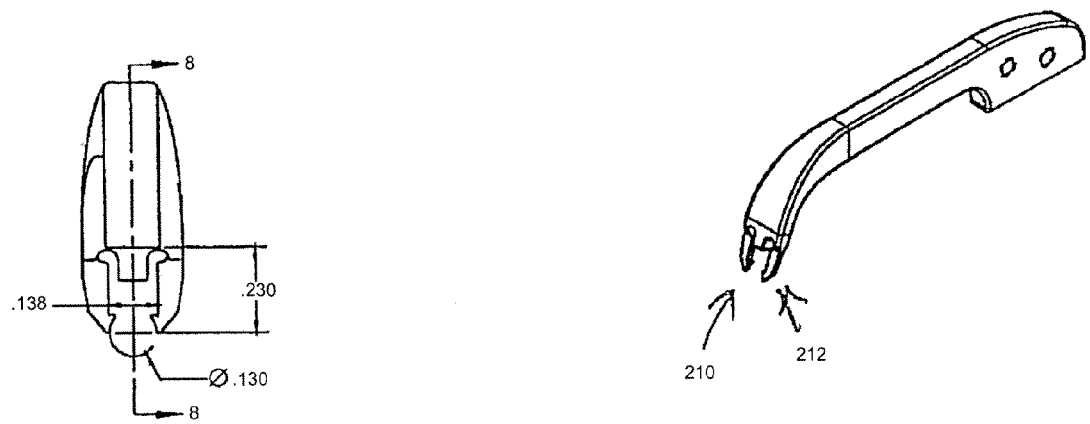
FIGURE 4 (Con't)

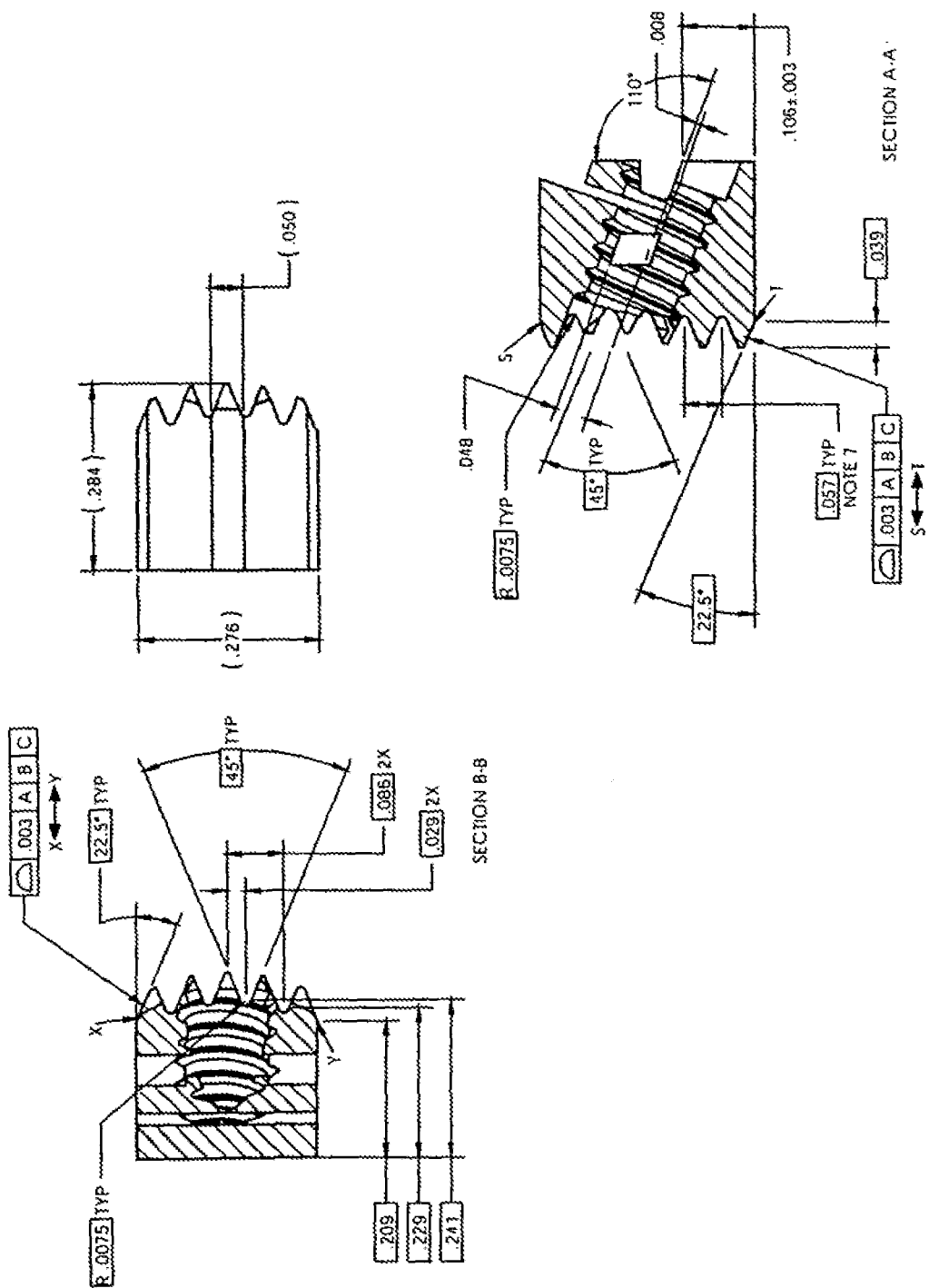
FIGURE 6 (Con't)

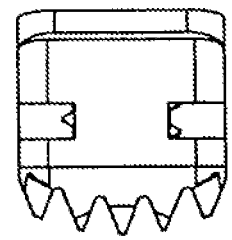
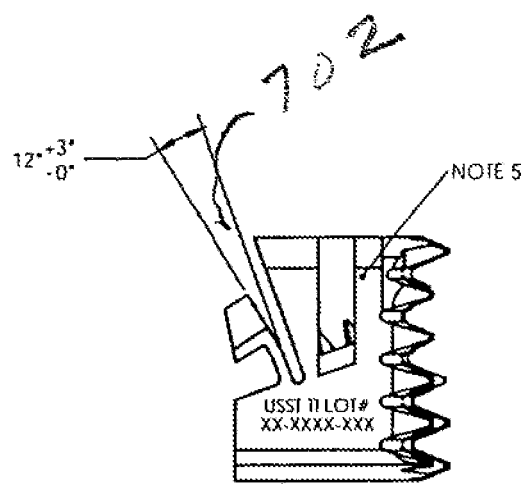
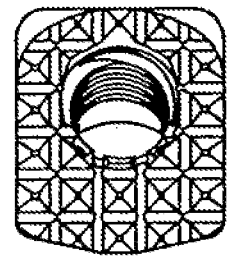
FIGURE 7 (Con't)

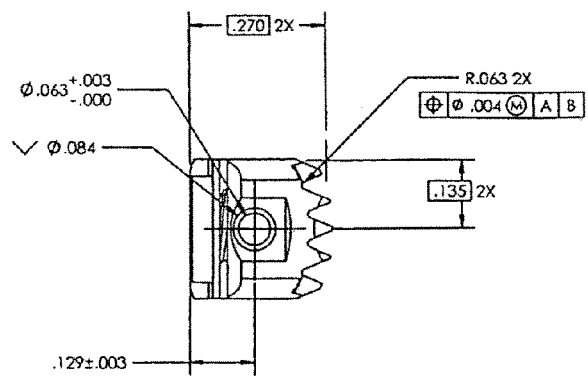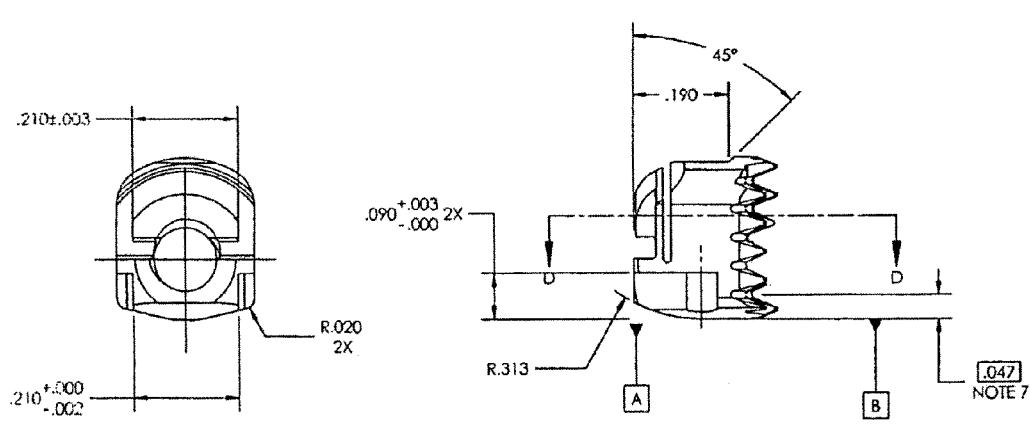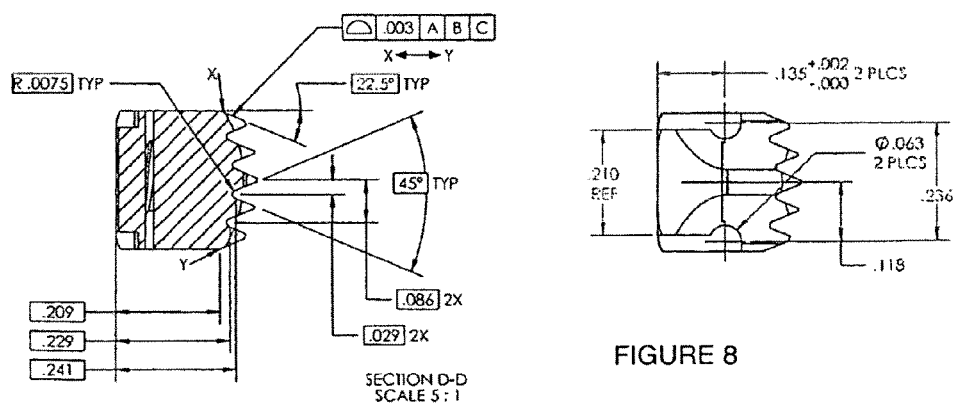
FIGURE 8

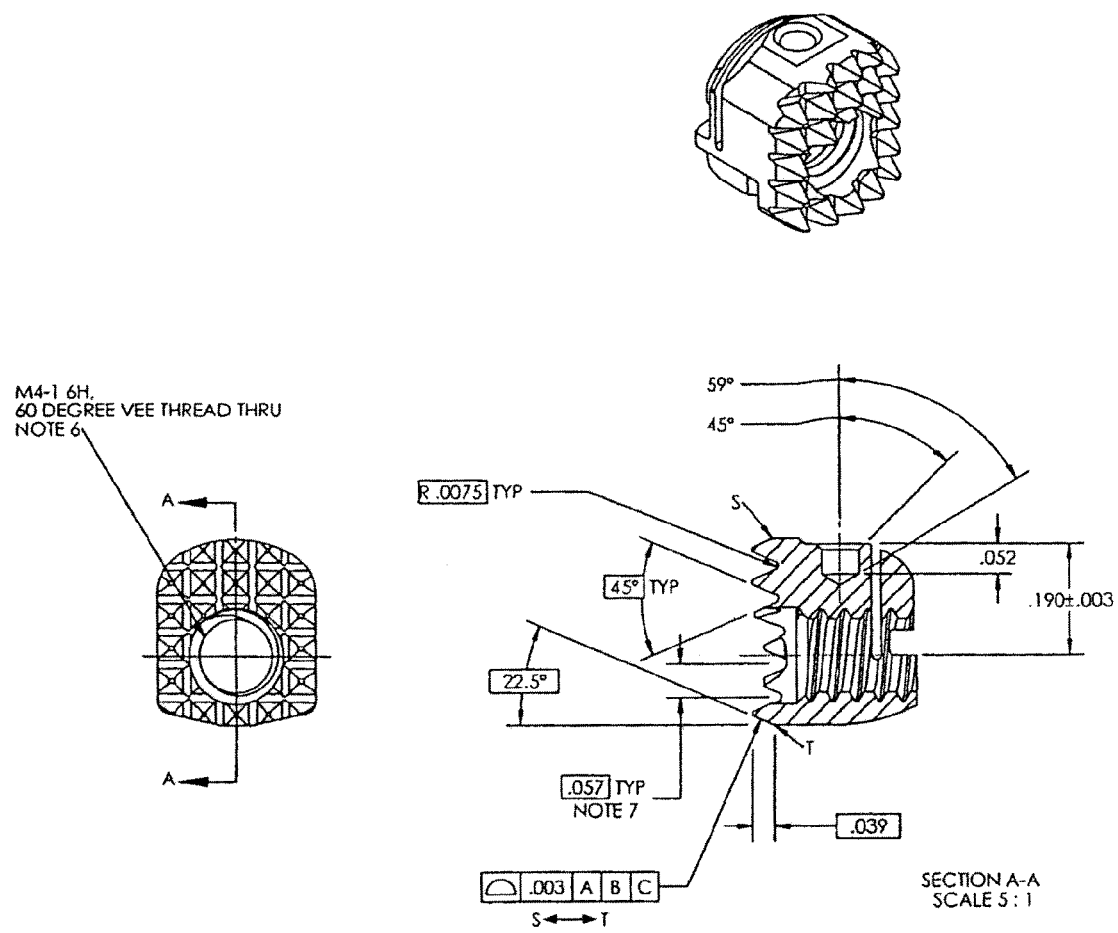
FIGURE 8 (Con't)

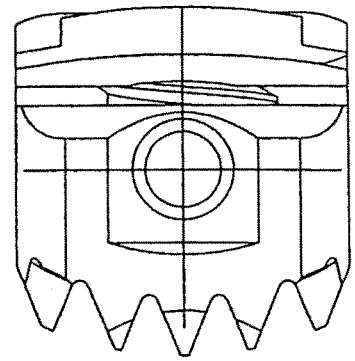
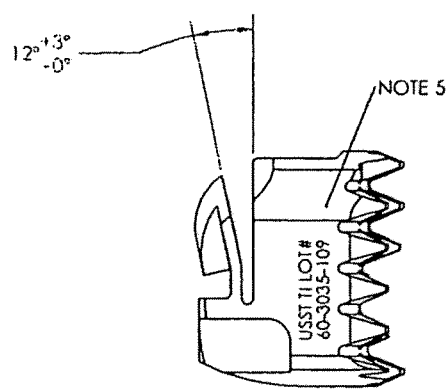
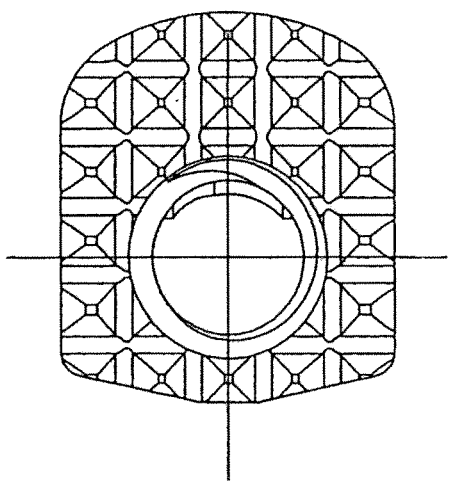
FIGURE 9 (Con't)

BONE FIXATION IMPLANT SYSTEM AND METHOD

REFERENCE TO RELATED APPLICATIONS

This application claims is a continuation of copending U.S. patent application Ser. No. 12/122,498, filed May 16, 2008, which is a continuation-in-part of U.S. patent application Ser. No. 10/973,524, filed Oct. 26, 2004 and now issued as U.S. Pat. No. 7,563,275, which is a continuation-in-part of U.S. patent application Ser. No. 10/683,076, filed Oct. 10, 2003 and now issued as U.S. Pat. No. 7,608,094, which claims priority to U.S. Provisional Patent Application Ser. No. 60/417,543, filed Oct. 10, 2002. Copending U.S. patent application Ser. No. 12/122,498 also claims priority to U.S. Provisional Patent Application Ser. No. 60/938,886, filed May 18, 2007. The entire contents of each of the foregoing applications is incorporated herein by specific reference.

FIELD OF THE INVENTION

This invention relates to bone arthrodesis, and more particularly to bone fixation implants and systems and methods for installing such implants.

BACKGROUND OF THE INVENTION

Bone arthrodesis or fusion is a process used to assist in the healing or stabilization of impaired bones or joints. In particular, facet arthrodesis is used to fuse the superior and inferior facet in spinal treatment operations, Prior art systems and methods have used bone screws which are screwed through the superior and inferior facets to immobilize the joint so as to permit the adjoined bone sections to fuse together. Wire has also been used to loop around the facets to immobilize the joint. The surgical procedures that must be performed to implant the screws or wires are difficult and time consuming. There is therefore a need for improved bone fixation implants, devices and methods.

SUMMARY OF THE INVENTION

This invention resides in a bone-fastening system. While the described embodiments are oriented toward direct facet fixation, one of skill in the art will appreciate that system and method may be modified for other applications, including translaminar facet fixation and the setting of fractures.

The system includes an implant with a threaded screw, a distal nut with a threaded bore, and a proximal washer which may also be threaded. An instrument for implanting the implant includes a handle and a barrel terminating in a holder for the washer. A c-shaped bridge assembly has a first end connected to the barrel and a second end including a holder for the nut in axial alignment with the washer. A manually operated control on the instrument, coupled to an elongated element in the barrel, causes the washer to move toward the nut, thereby applying compressive pressure to bone portions to be fastened together. A drive mechanism disposed within the barrel has a distal end with a holder for the screw and a proximal end that is turned by a user, thereby advancing the screw through the washer to the nut to fasten the bone portions under compression. A separate control is used to release pressure on the elongated element in the barrel, enabling the implant to be easily removed from the implant once in position.

In the preferred embodiment, the controls are triggers that are squeezed toward the handle by a user. The nut may include opposing side cut-outs that extend into the threaded bore, and the holder for the nut may include a pair of opposing side tabs that engage with the cut-outs during placement of the nut. The opposing side tabs are deformed outwardly when the screw is advanced through the nut, thereby enabling the bridge assembly to be remove from the implant. The nut may further include opposing side cut-outs that do not extend into the threaded bore, with the holder for the nut include a pair of opposing outriggers that engage with the cut-outs to enhance stability placement and fastening of the nut.

The holder for the washer may be coupled to a manually operated control enabling a user to orient the washer for improved conformity with a bony surface. In the preferred embodiment, the screw includes a pointed tip that self-taps through bone, and the nut and washer nut and washer have differently angled bone-contacting surfaces with bone-penetrating spikes, neither of the surfaces being perpendicular to the alignment axis.

BRIEF DESCRIPTION OF THE DRAWINGS

FIG. 1A is a side view of a facet gun according to this invention;
FIG. 1B is a front view of the facet gun of FIG. 1A;
FIG. 1C is a side view of the facet gun with a cover removed showing internal mechanisms;
FIG. 1E is a top view of the facet gun of FIG. 1A;
FIG. 2A is a side view drawing of the transfacet barrel/screw/nut/washer assembly;
FIG. 2B is a bottom view drawing of the assembly of FIG. 2A;
FIG. 2C is a top view drawing of the assembly of FIG. 2A with parts indicated;
FIG. 2D is an oblique view drawing of the assembly of FIG. 2A;
FIG. 2E is a front view drawing of the assembly of FIG. 2A;
FIG. 2F is a back view drawing of the assembly of FIG. 2A;
FIG. 8 shows different views of a PCS nut.

DETAILED DESCRIPTION OF THE PREFERRED EMBODIMENTS

U.S. Pat. No. 7,563,275 titled "Bone Fixation Implant System and Method," the entire contents of which are incorporated herein by reference, describes a bone fixation implant system and method particularly useful for percutaneous facet fixation during minimally invasive surgical procedures. The system includes an implant for bone arthrodesis and a bone fastening device. The implant includes a fastener with an elongated shaft having a head at one end and a bone-piercing point at the opposite end. A first washer has structure for engaging the head of the shaft so as to be polyaxially pivotable with respect to the head. A locking member has structure for engaging the shaft. The locking member can have a second washer pivotally engaged thereto. The bone fastening device can include an elongated cannula with a collet for detachably engaging the first washer and for advancing the first washer. Structure is provided for engaging the fastener and for advancing and rotating the fastener through the collet and through the first washer. The bone arthrodesis device further includes a lower end portion extending from the cannula. The lower end portion has structure for detachably engaging the locking member. The fastener, first washer, and locking member are aligned such that the advancing fastener will advance through the first washer, drill through the bone, and move into the locking member. A method for performing bone arthrodesis is also disclosed.

Figure 1D:
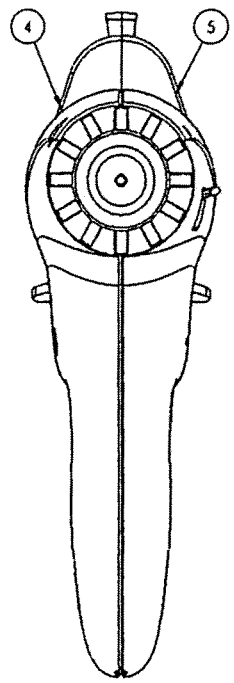
FIG. 1D is a back view of an improved facet gun according to the invention.
Figure 1F:
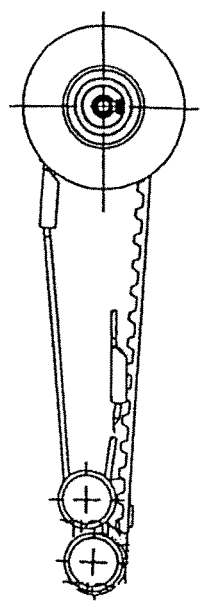
FIG. 1F is a cross-section view of the facet gun of FIG. 1A.

The following description details improvements to facet fixation apparatus and methods, including the system and methods set forth in application Ser. No. 10/973,524 referenced above. FIG. 1A is a side view of an improved facet gun described in U.S. Provisional Application Ser. No. 60/938,886, the entire content of which is also incorporated herein by reference. FIG. 1B is a front view. FIG. 1C is a side view with a cover removed showing internal mechanisms. FIG. 1D is a back view, FIG. 1E is a top view, and FIG. 1F is a cross-section. As with the gun described in the '524 application, the fastener is driven with handle 102 which makes a ratcheting connection through the mechanism depicted in the cross-section of FIG. 1F. An improvement is tab 100 which is coupled to the washer described in further detail below. Right-left movement of the tab 100 also moves the washer slightly clockwise and counter-clockwise, thereby providing improved orientation of the washer relative to recipient bone-engagement surfaces.

FIG. 2A is a side view drawing of a disposable barrel assembly 200 that mounts to the gun body of FIG. 1 by way of threaded coupler 202. FIG. 2B is a bottom view, FIG. 2C is a top view, FIG. 2D is an oblique view, FIG. 2E is a front view, and FIG. 2F is a back view. These figures show the barrel assembly without the screw, nut or washers in position. One improvement over previous designs is the provision of distal prongs 210, 212, which fit into slots in the nut described below. These prongs, which are separated by the advancing fastener, hold the distal implant components in position until the fastener is advanced.

Figure 3A:
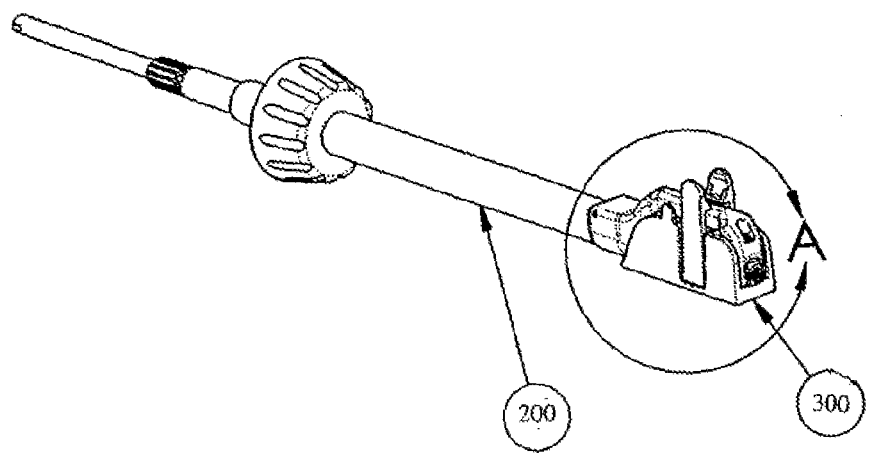
FIG. 3A is an oblique drawing of a transfacet barrel assembly with a retainer in place.
Figure 3B:
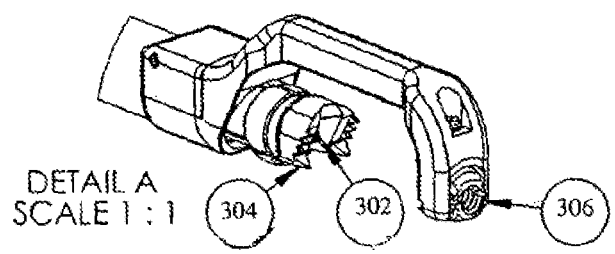
FIG. 3B is an oblique drawing of the distal end of transfacet barrel assembly the retainer removed showing the screw, washer and nut.

FIG. 3A is an oblique drawing of the transfacet barrel assembly with a temporary retainer 300 in place. FIG. 3B is an oblique drawing of the distal end of the barrel assembly with the retainer removed showing the screw 302, washer 304 and nut 306.

Figure 4:
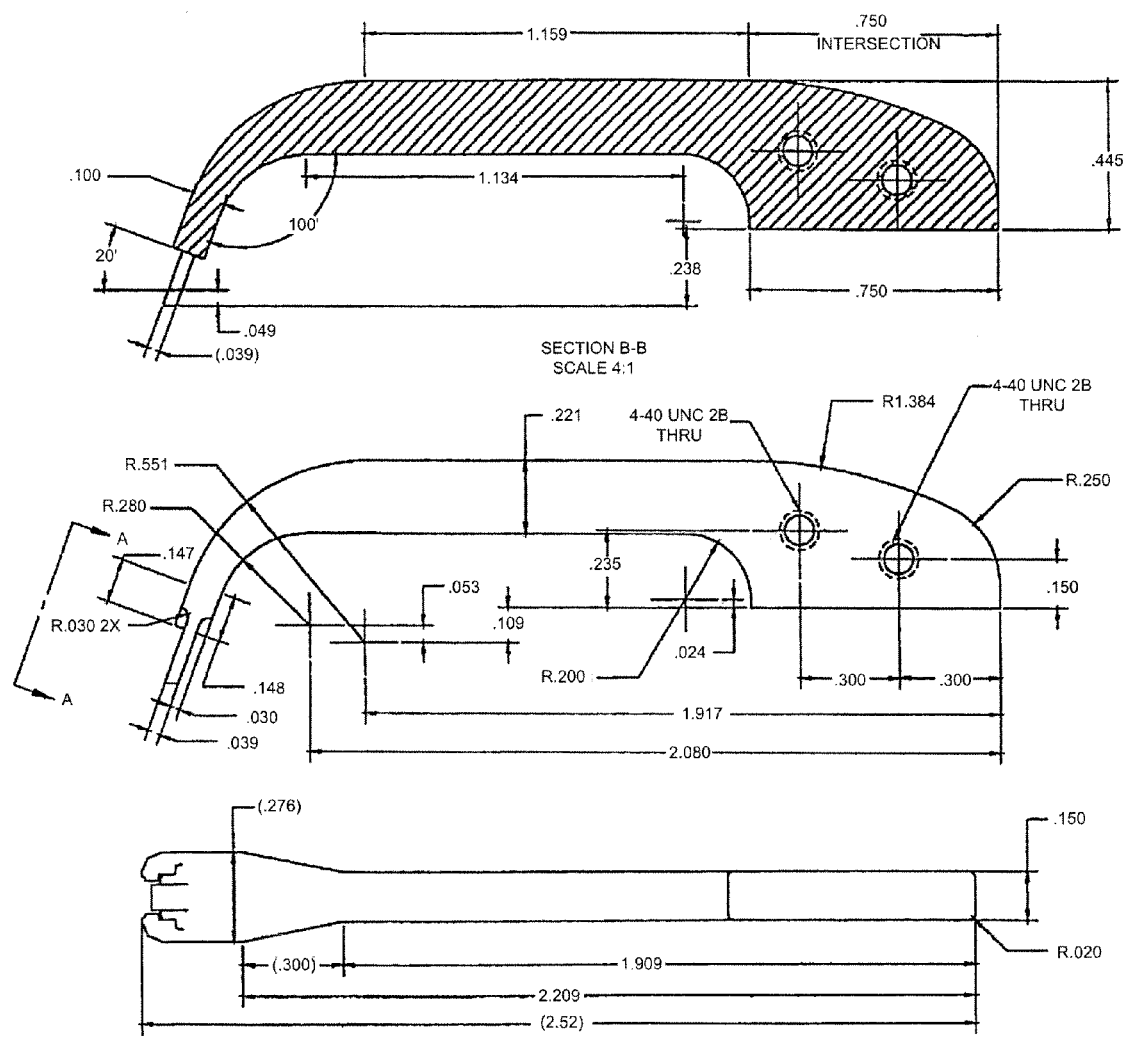
FIG. 4 shows different views of a bridge finger release.
Figure 5:
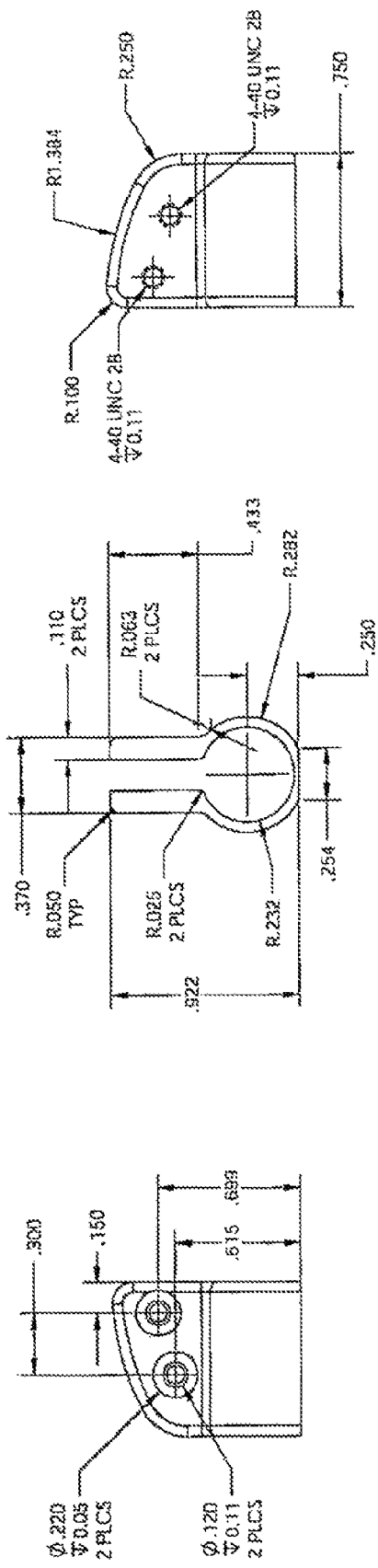
FIG. 5 shows different views of a bridge mount.
Figure 6:
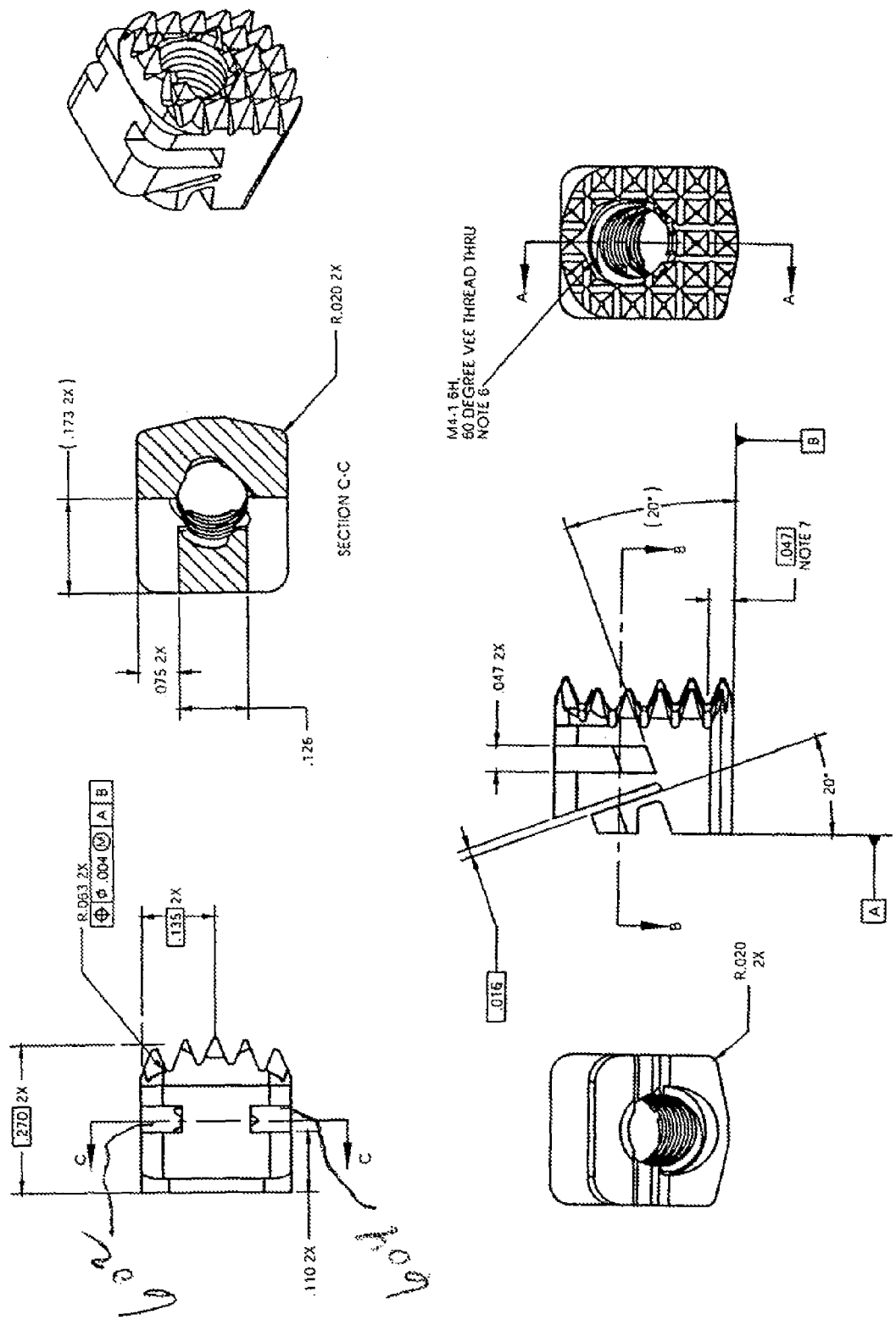
FIG. 6 shows different views of a flap nut parallel convex finger.
Figure 7:
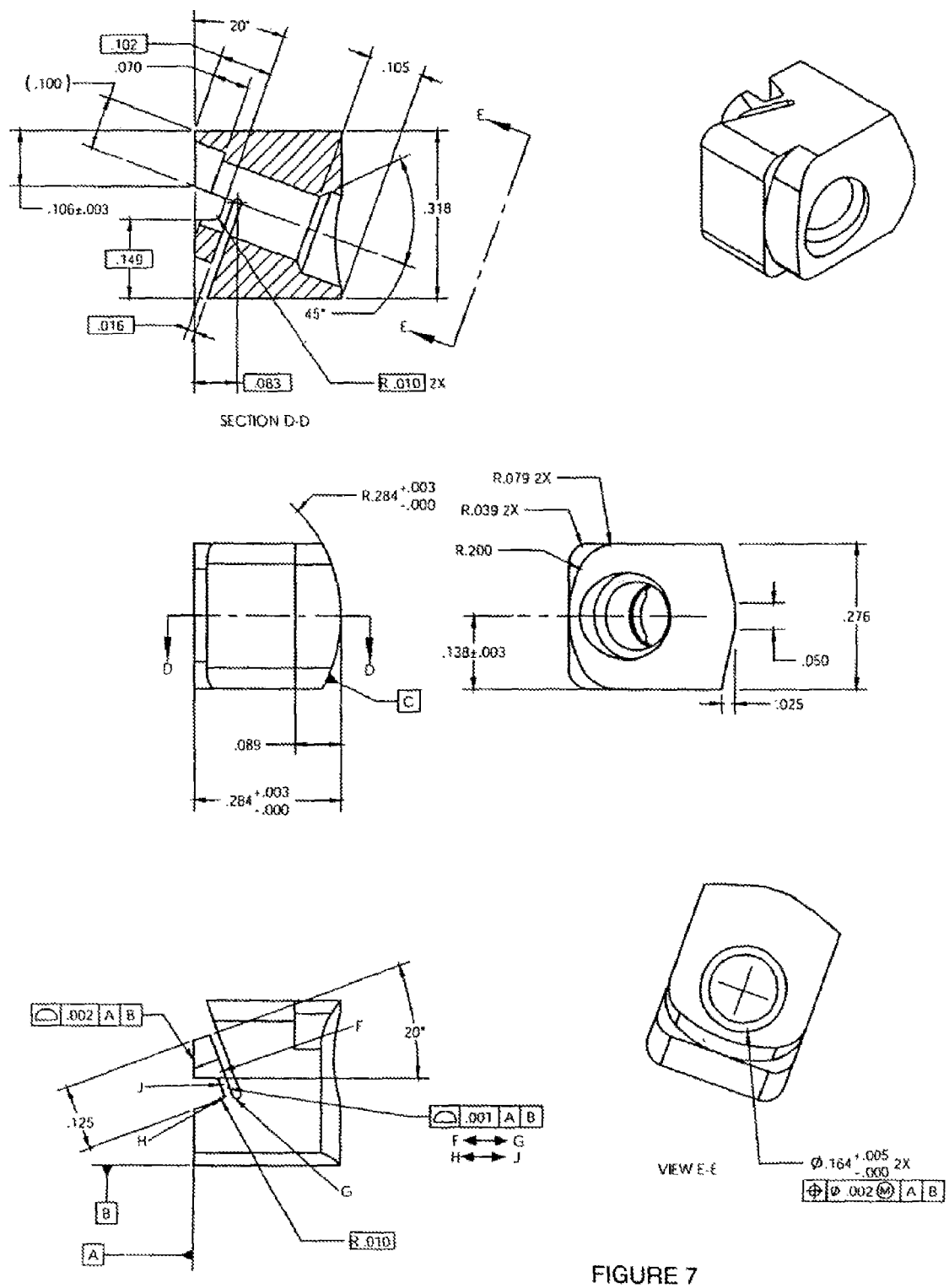
FIG. 7 shows blank and deformed processes.
Figure 9:
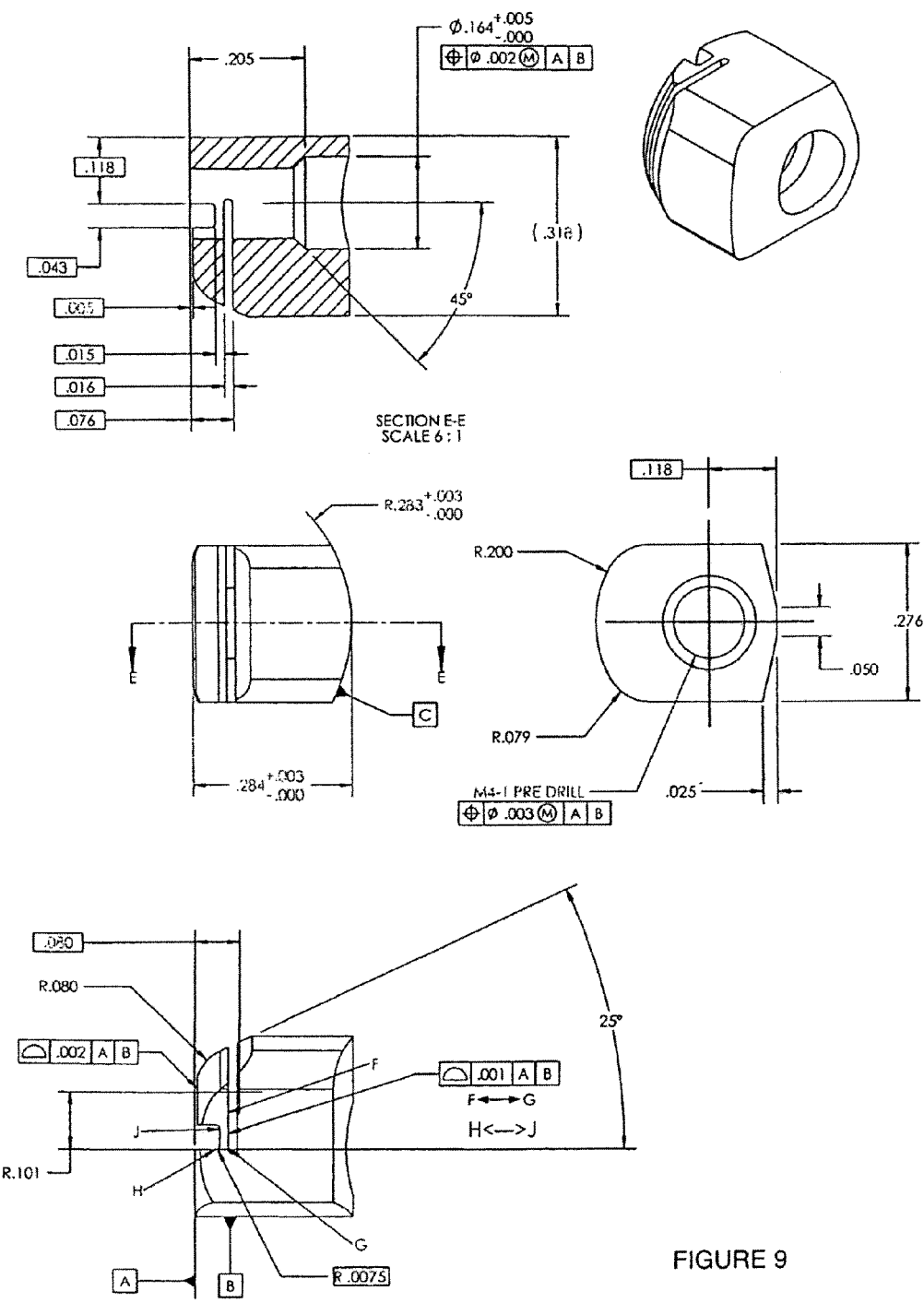
FIG. 9 shows a different set of blank and deformed processes.
Figure 10:
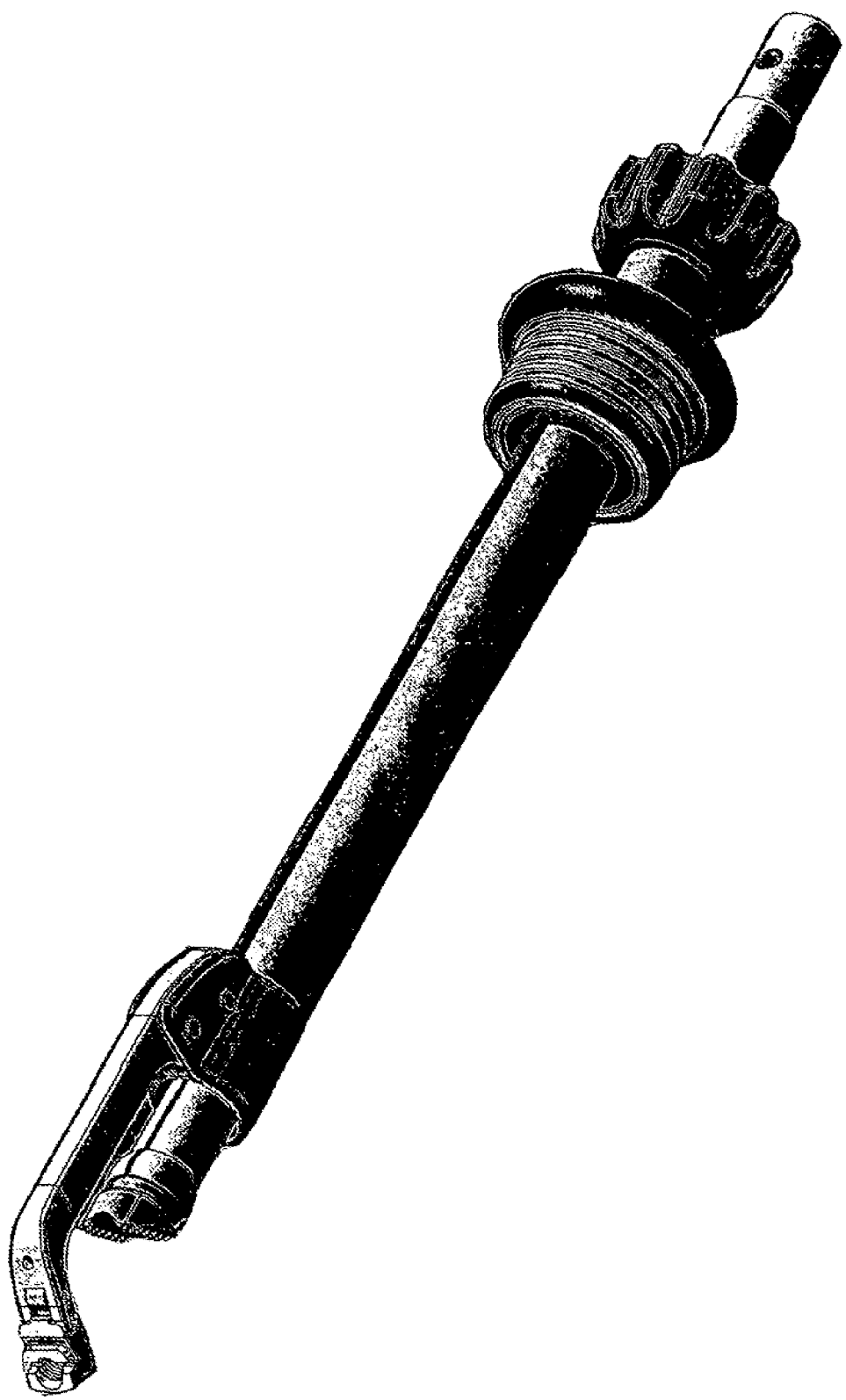
FIG. 10 is an oblique drawing which shows a barrel assembly finger release.

FIG. 4 shows different views of a bridge finger release, better illustrating spreadable prongs 210, 212. FIG. 5 shows different views of a bridge mount, and FIG. 6 shows different views of a flap nut. These drawings better illustrate side slots 602, 604 which receive prongs 210, 212. FIG. 7 shows a blank version of the nut of FIG. 6 and a deformed version wherein slot 702 is spread prior to use. With this design, the advancing screw straightens the deformation back out with a residual interference that locks the two components in position. FIG. 8 shows different views of a PCS nut, and FIG. 9 shows blank and deformed processes. FIG. 10 is an oblique drawing which shows the barrel assembly with nut and washer in position.

Figure 11:
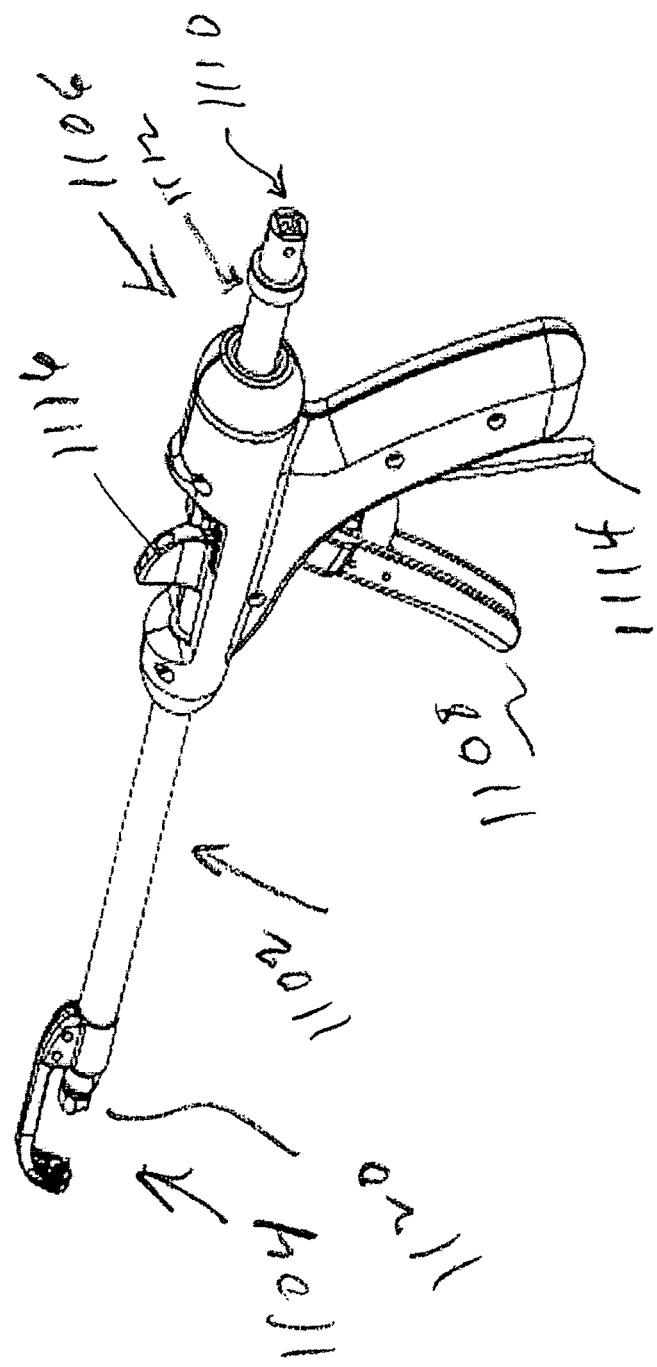
FIG. 11 is an oblique back view of a further improved facet gun apparatus according to the invention.

FIG. 11 is an oblique back view of a further improved facet gun apparatus according to the invention. In this case, the barrel assembly 1102 including bridge assembly 1104 is permanently affixed to the body of the gun 1106. This is not necessary to the invention, however, as it is contemplated to have bridge assembly preloaded with fasteners, enabling the bridge assembly and fasteners to become coupled to a barrel assembly and gun which is not disposable. In the case of FIG. 11, however, all components being integrally fabricated results in a disposable item.

Continuing the reference to FIG. 11, handle 1108 is used to compress the proximal washer against the distal nut, with the advancement of the screw being done manually by coupling a suitable drive instrument to socket 1110. This not only simplifies the overall design, but provides the surgeon with tactile feedback as to the extent of screw advancement, thereby minimizing over-tightening. Further improvements includes the provision of a hard stop 1112 on the proximal drive end, causing advancement to be terminated at a certain extent, thereby further minimizing over-tightening situations.

Continuing the reference to FIG. 11, the further improvements in the design is the provision of a release lever 1114, which disengages handle 1108, allowing the bridge to be removed from the fastened implant once secured in position. The design continues to incorporate tab 1116, which allows washer 1120 to rock back and forth for better cooperation with patient physiology.

Figure 12:
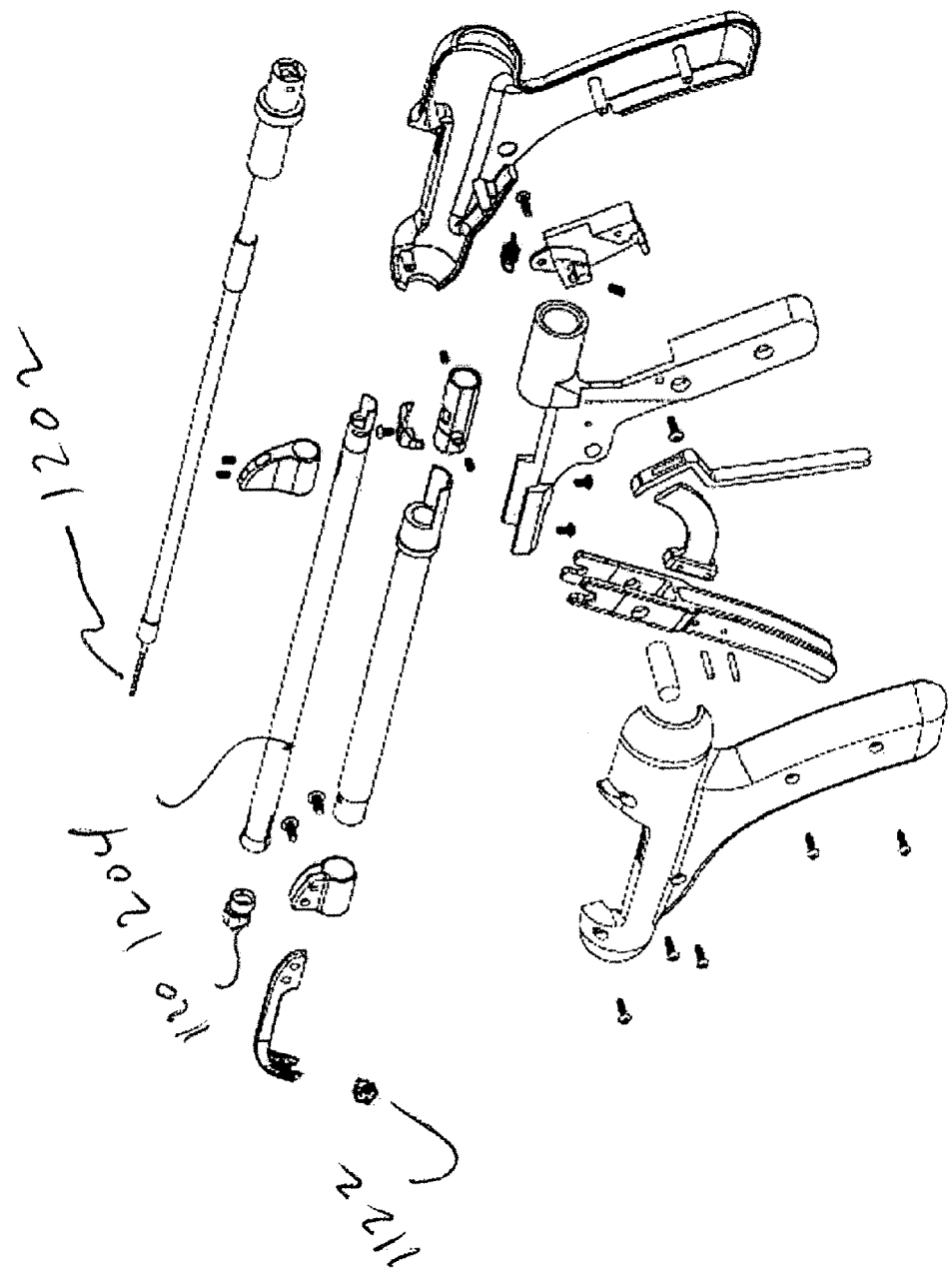
FIG. 12 is an exploded view of the instrument of FIG. 11.
Figure 13A:
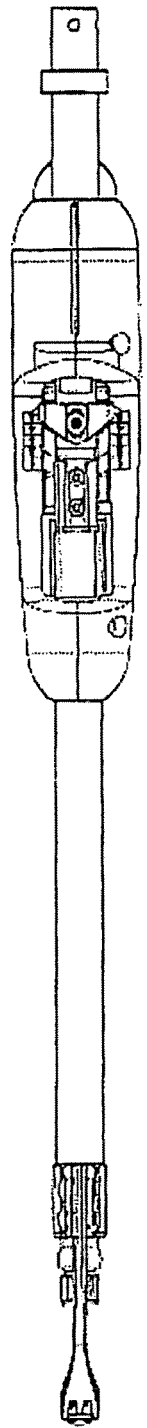
FIG. 13A is a top-down view of the gun depicted in FIGS. 11 and 12.
Figure 13B:
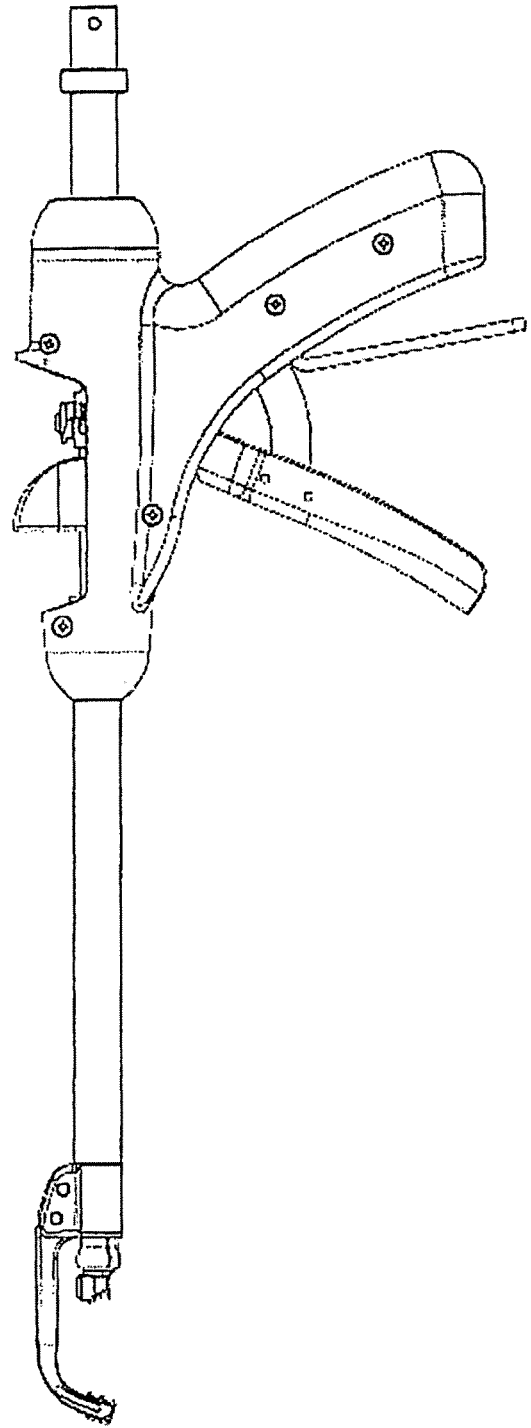
FIG. 13B is a side view of the gun depicted in FIGS. 11 and 12.
Figure 13C:
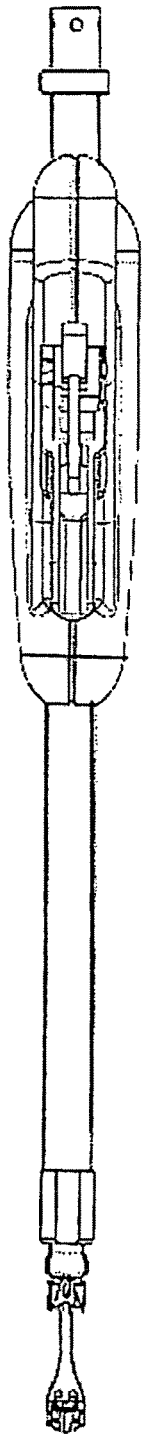
FIG. 13C is a bottom view of the gun depicted in FIGS. 11 and 12.
Figure 13E:
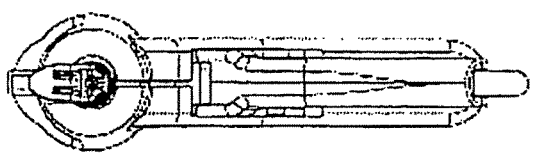
FIG. 13E is a front view of the gun depicted in FIGS. 11 and 12.
Figure 13D:
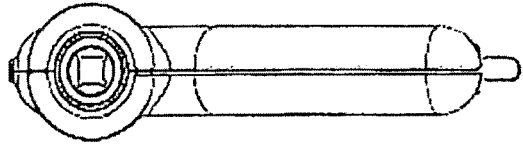
FIG. 13D is a back view of the gun depicted in FIGS. 11 and 12
Figure 14A:
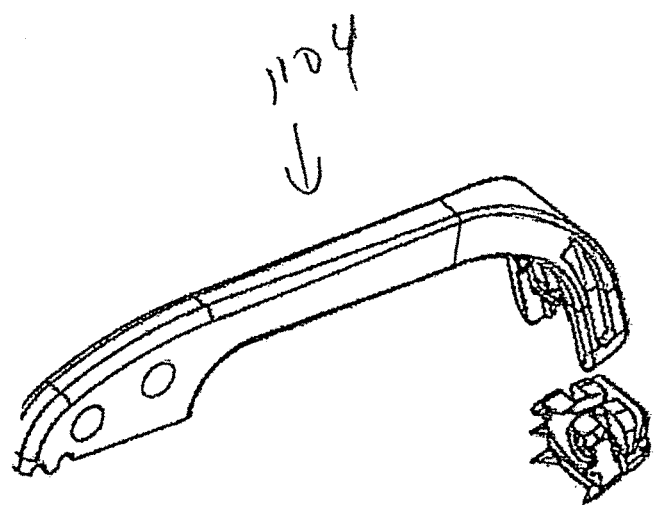
FIG. 14A is an oblique, exploded view of the bridge assembly from a rearward perspective.
Figure 14B:
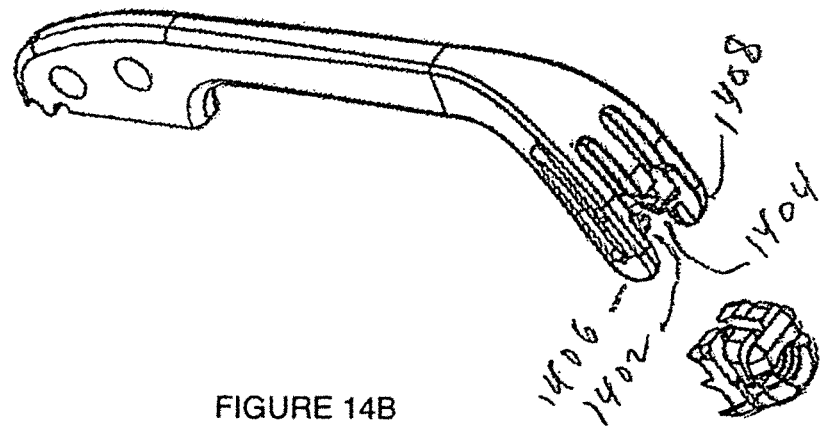
FIG. 14B is an oblique representative from a front perspective of the bridge assembly from a rearward perspective.
Figure 14C:
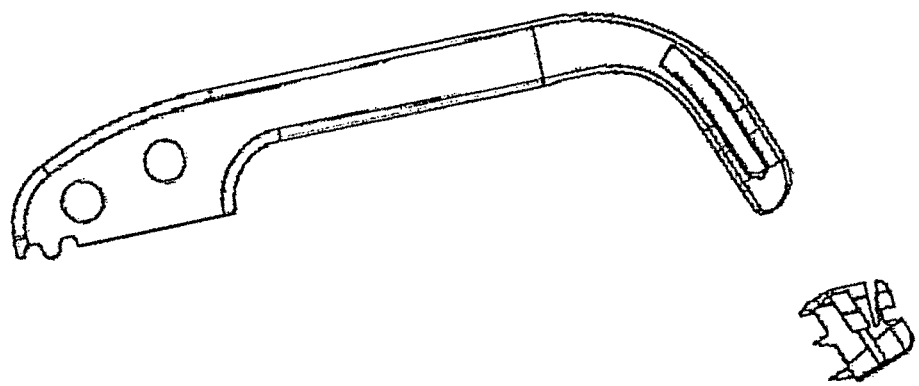
FIG. 14C is a side view of the bridge assembly from a rearward perspective.

FIG. 12 is an exploded view of the instrument of FIG. 11, showing how far fewer components are necessary, as compared to previous designs. With the use of a manually-operated mechanism to advance screw 1202, the need for complex ratcheting mechanisms has been eliminated. FIG. 12 also better illustrates cupola tube 1204, which is the element used to apply pressure to washer 1120 against nut 1122. FIG. 13A is a top-down view of the gun depicted in FIGS. 11 and 12. FIG. 13B is a side view; FIG. 13C is a bottom view; FIG. 13D is a back view; and FIG. 13E is a front view. FIG. 14A is an oblique, exploded view of the bridge assembly 1104 from a rearward perspective. FIG. 14B is an oblique representative from a front perspective, and FIG. 14C is a side view. The design continues to incorporate prongs 1402, 1404 which engage with indents in the nut and spread with advancement of the screw. However, an improvement includes outriggers 1406, 1408 which do not expand. This facilitates a straightforward release of the bridge assembly from the nut once in position, while maintaining stability and controlled movement of the gun overall.

Figure 15:
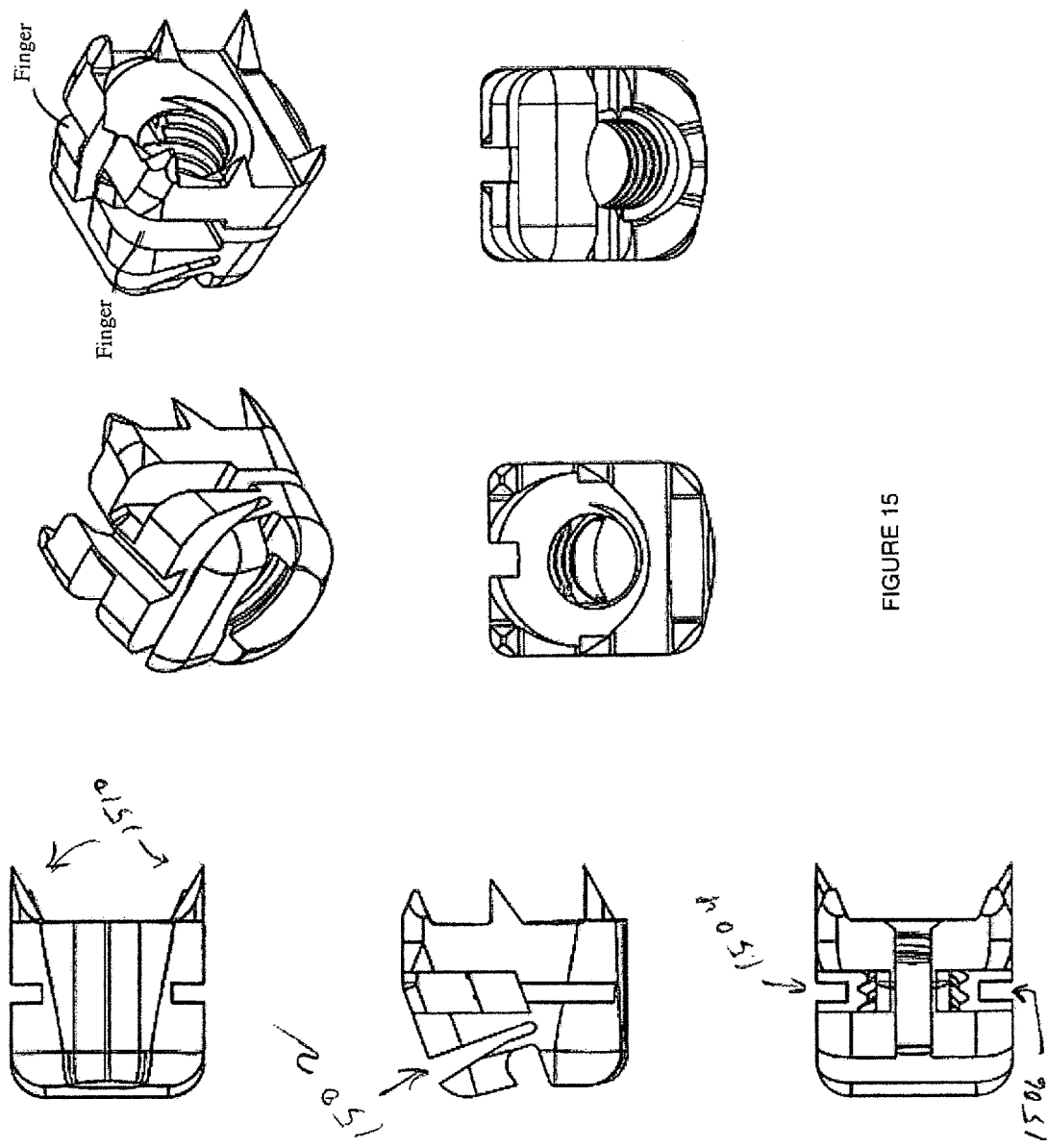
FIG. 15 provides different views of an improved nut according to the invention.
Figure 16A:
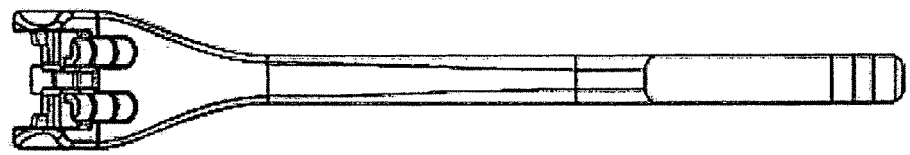
FIG. 16A is a bottom view of the improved bridge assembly.
Figure 16B:
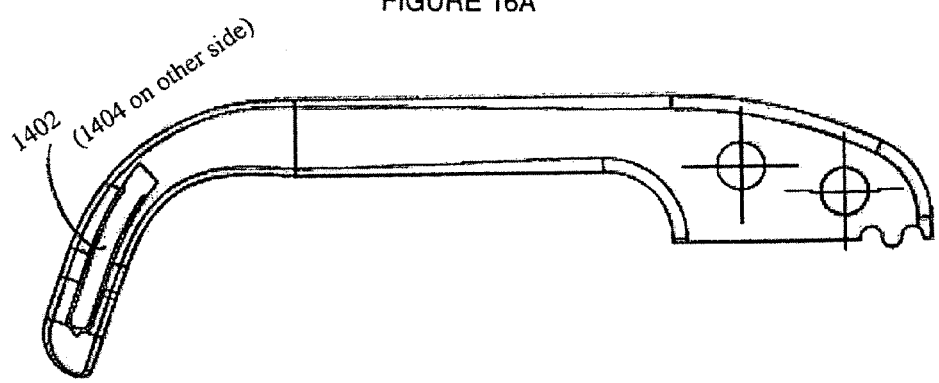
FIG. 16B is a side view of the improved bridge assembly.
Figure 16C:
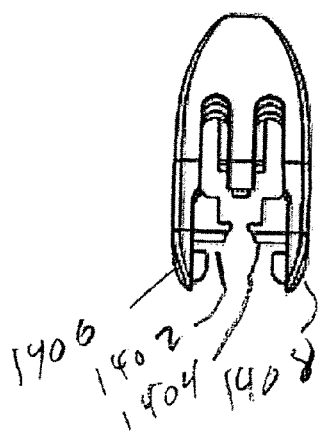
FIG. 16C is a front view of the improved bridge assembly.
Figure 16D:
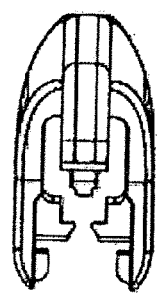
FIG. 16D is a back view of the improved bridge assembly.
Figure 17A:
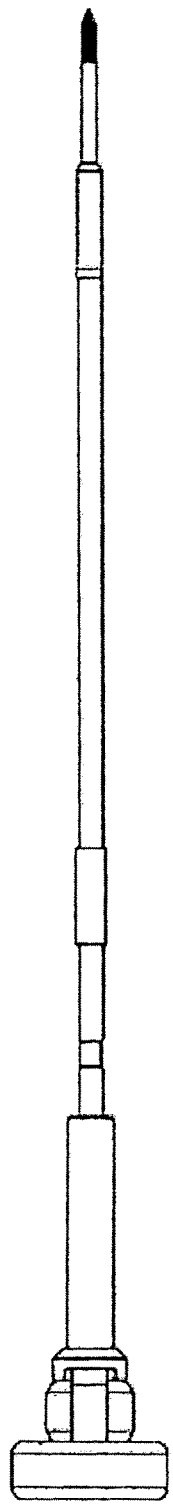
FIG. 17A is one view of an improved driver according to the invention.
Figure 17B:
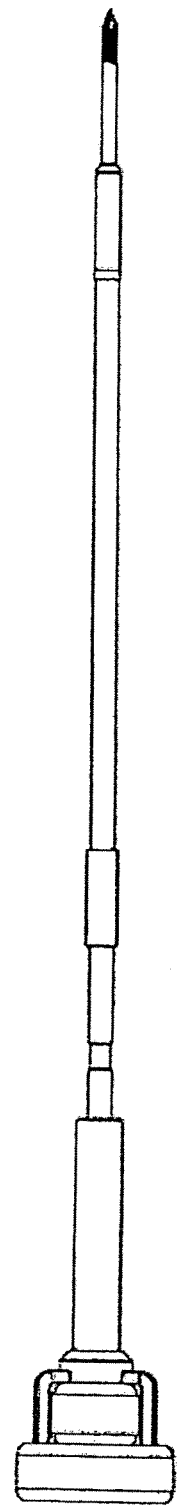
FIG. 17B is a different view of the improved driver.
Figure 17C:
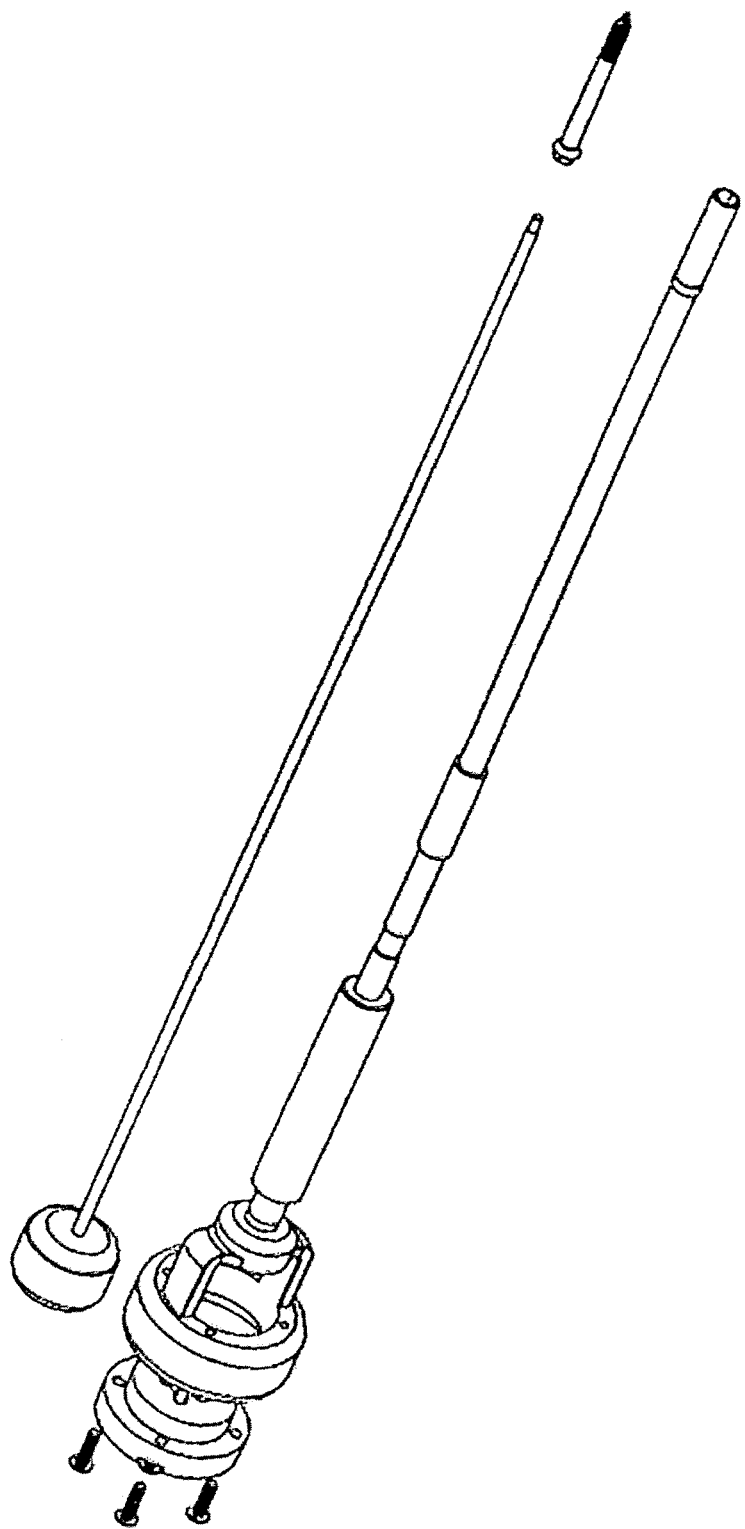
FIG. 17C is an exploded isometric drawing of the driver assembly.
Figure 18:
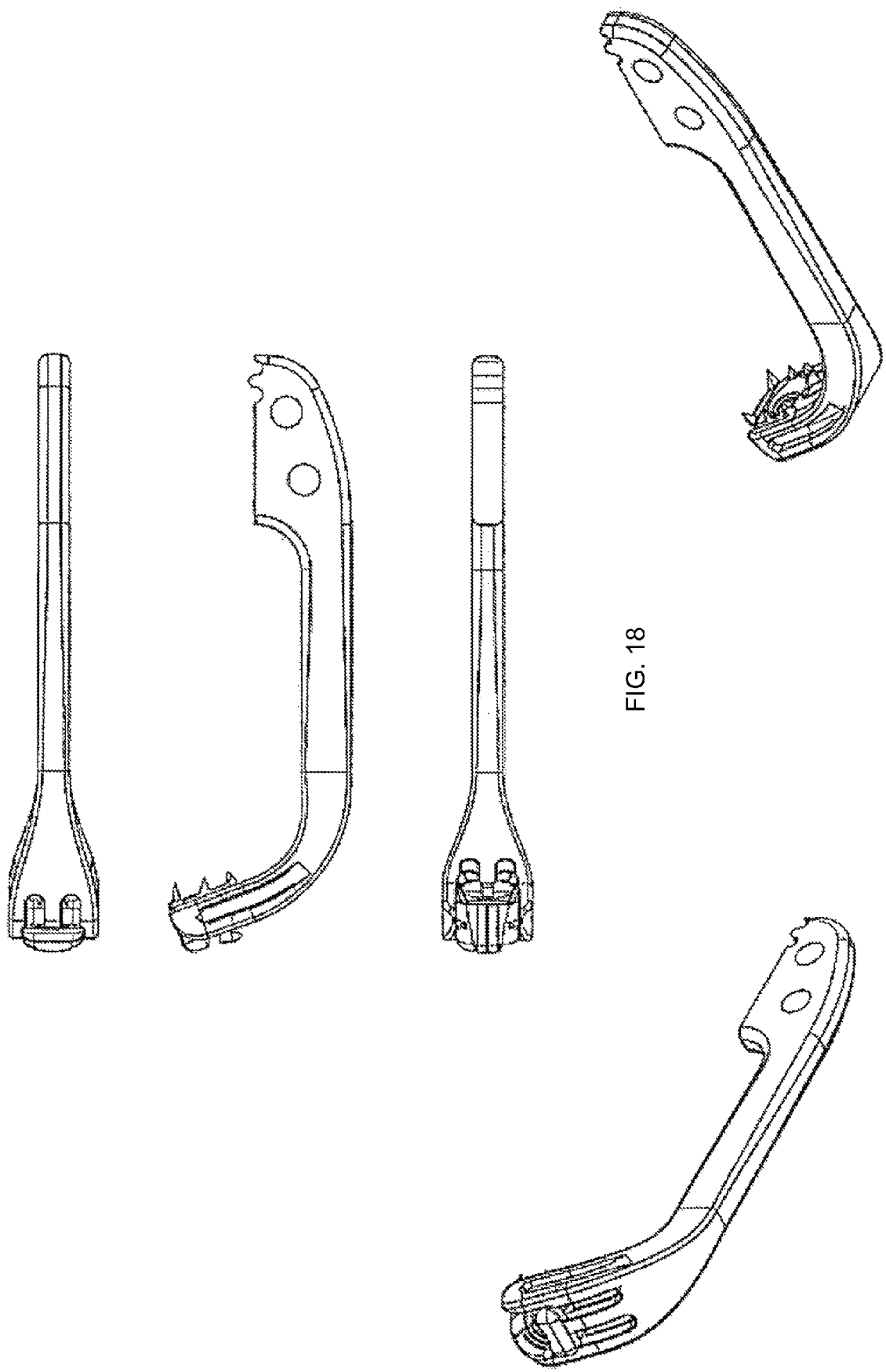
FIG. 18 shows the bridge assembly from different perspectives, with the distal nut in position.

FIG. 15 provides different views of an improved nut according to the invention. Slot 1502 engages with the outriggers just described, whereas intents 1504, 1506 are used to receive the prongs 1402, 1404. Note that the threads are visible through these intends, which is the reason why the prongs are moved apart as the screw is advanced. Further improvement is the use of differently positioned and extended fangs 1510, which facilitate better penetration and fixation. FIG. 16A is a bottom view of the improved bridge assembly; FIG. 16B is a side view; FIG. 16C is a front view; and FIG. 16D is a back view. These views better show outriggers 1406, 1408 and spreadable fingers 1402, 1404. FIG. 17A is one view of an improved driver according to the invention, and FIG. 17B is a different view of that improved driver. In contrast to previous designs, which required a two-part installation process, this improved driver allows for a one-step assembly and use process. The driver simply slides into position, enabling the practitioner to immediately begin the threading operation. FIG. 17C is an exploded isometric drawing of the driver assembly. FIG. 18 shows the bridge assembly from different perspectives, with the distal nut in position.

We claim:

1. A bone fastening instrument, comprising:
    a handle;
    a barrel assembly connected to the handle;
    a bridge assembly connected to the barrel assembly, wherein the bridge assembly is configured to receive and engage a first connector element, and wherein the bridge assembly is configured to receive and engage a second connector element in axial alignment with the first connector element so as to allow for receipt of a fastening element between the first and second connector elements;
    a control configured to, upon actuation, approximate the first connector element and the second connector element so as to apply compressive pressure to bone portions positioned between the first connector element and the second connector element; and
    a drive mechanism configured to advance the fastening element through the bone portions and connect the first connector element with the second connector element to fasten the bone portions under compression.

2. The bone fastening instrument of claim 1, wherein the fastening element comprises a threaded screw.

3. The bone fastening instrument of claim 1, wherein the bridge assembly comprises the first connector element and the second connector element.

4. The bone fastening instrument of claim 3, wherein the first connector element comprises a washer.

5. The bone fastening instrument of claim 4, wherein the washer comprises a plurality of bone-penetrating spikes.

6. The bone fastening instrument of claim 3, wherein the second connector element comprises a nut.

7. The bone fastening instrument of claim 6, wherein the nut comprises at least one fang configured to engage one of the bone portions.

8. The bone fastening instrument of claim 1, wherein the bridge assembly comprises a first arm and a second arm position opposite from the first arm.

9. The bone fastening instrument of claim 8, wherein the first arm comprises at least two outriggers configured to engage opposite sides of the first connector element.

10. The bone fastening instrument of claim 9, wherein the first arm comprises at least one prong configured to engage a slot in the first connector element.

11. The bone fastening instrument of claim 10, wherein the first connector element comprises a nut.

12. The bone fastening instrument of claim 11, wherein the second arm is configured to engage the second connector element.

13. The bone fastening instrument of claim 1, wherein the bridge assembly comprises a c-shaped bridge assembly having a first end connected to the barrel assembly and a second end including a holder for the second connector element in axial alignment with the first connector element.

14. The bone fastening instrument of claim 1, wherein the control is configured for manual operation.

15. The bone fastening instrument of claim 14, wherein the control comprises a trigger that is configured to be squeezed toward the handle by a user.

16. The bone fastening instrument of claim 1, further comprising a second control configured to release the bridge assembly from the first and second connecting elements.

17. The bone fastening instrument of claim 16, wherein the second control comprises a release lever.

18. The bone fastening instrument of claim 17, wherein the release lever is positioned in between the handle and the control.

19. A bone fastening system, comprising:
    a handle;
    a barrel assembly connected to the handle;
    a bridge assembly connected to the barrel assembly, wherein the bridge assembly comprises:
        a first connector element;
        a second connector element in axial alignment with the first connector element; and
        a fastening element configured to be inserted through the first connector, through at least two bone portions, and through the second connector element;
    a control configured to, upon actuation, approximate the first connector element and the second connector element so as to apply compressive pressure to the at least two bone portions positioned between the first connector element and the second connector element; and
    a drive mechanism configured to advance the fastening element through the bone portions to connect the first connector element with the second connector element and fasten the bone portions under compression, wherein the control is configured to allow for application of compressive pressure to the at least two bone portions prior to advancing the fastening element to connect the first connector element with the second connector element such that the bone portions can be fastened under compression.

* * * * *